United States Patent [19]

Weiss

[11] Patent Number: 4,880,412

[45] Date of Patent: Nov. 14, 1989

[54] TUBE INSERTION APPARATUS

[76] Inventor: Sol Weiss, 17227 Quesan Pl., Encino, Calif. 91316

[21] Appl. No.: 153,934

[22] Filed: Feb. 9, 1988

[51] Int. Cl.⁴ .............................................. A61M 5/00
[52] U.S. Cl. ................................... 604/165; 604/164; 604/177
[58] Field of Search ....... 128/305.3, 200.26, DIG. 26; 604/158, 161, 164, 165, 177

[56] References Cited

U.S. PATENT DOCUMENTS

| | | | |
|---|---|---|---|
| 4,326,519 | 4/1982 | D'Alo et al. | 604/165 |
| 4,445,893 | 5/1984 | Bodicky | 604/177 |
| 4,520,810 | 6/1985 | Weiss | 128/305.3 |

Primary Examiner—Michael H. Thaler
Assistant Examiner—William Lewis
Attorney, Agent, or Firm—Gerald L. Price

[57] ABSTRACT

Apparatus for inserting tubes of varying sizes, such as catheter tubes, into a patient including mating upper and lower needle portions, the lower portion being flattened on the bottom surface for abutment with the body of the patient with tabs extending outwardly on both sides of the mating portions also adapted to abut against the body of the patient. The two mating portions are removably secured together so that the mating needle halves form an elongated cylindrical needle extending outwardly form one side of the secured portions and the mating portions forming a slot on the other side for receiving the luer adapter of a stylet therein.

18 Claims, 12 Drawing Sheets

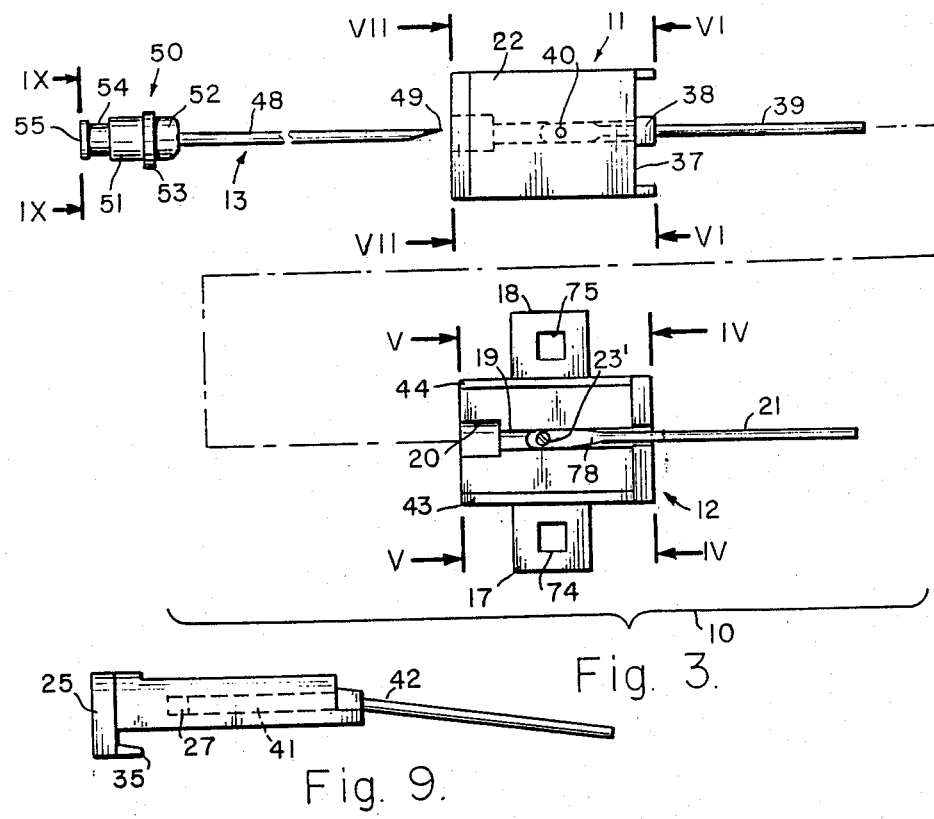
Fig. 3.
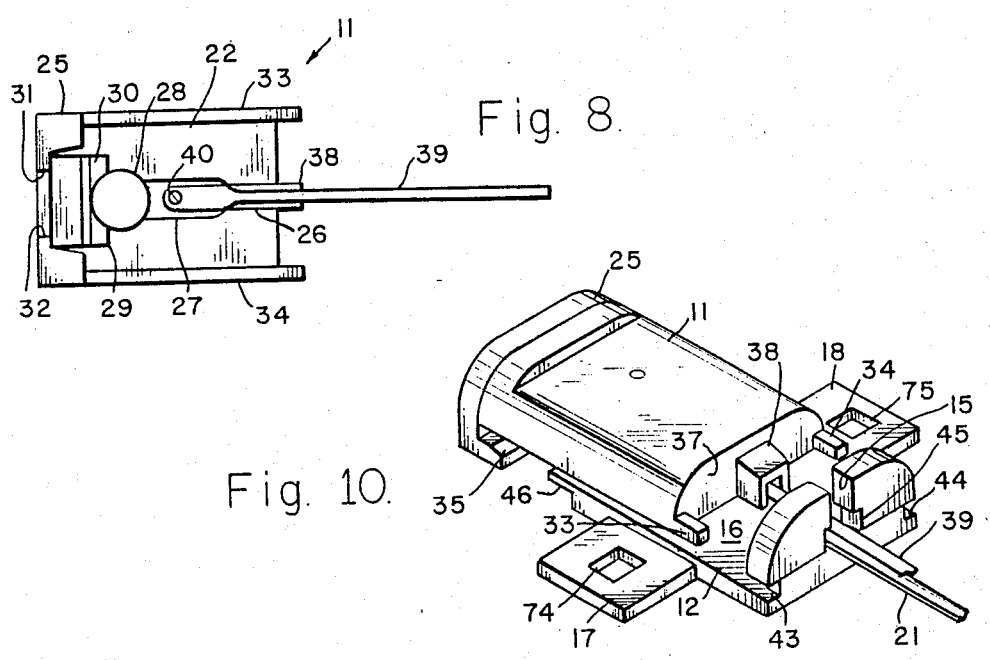
Fig. 9.
Fig. 8.
Fig. 10.

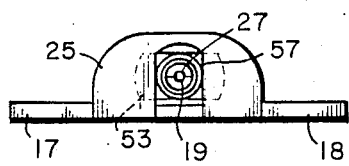
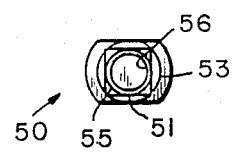
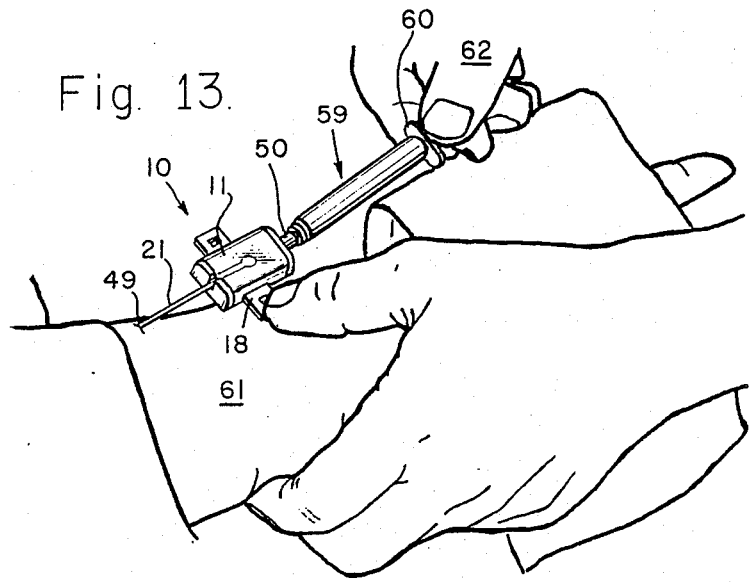
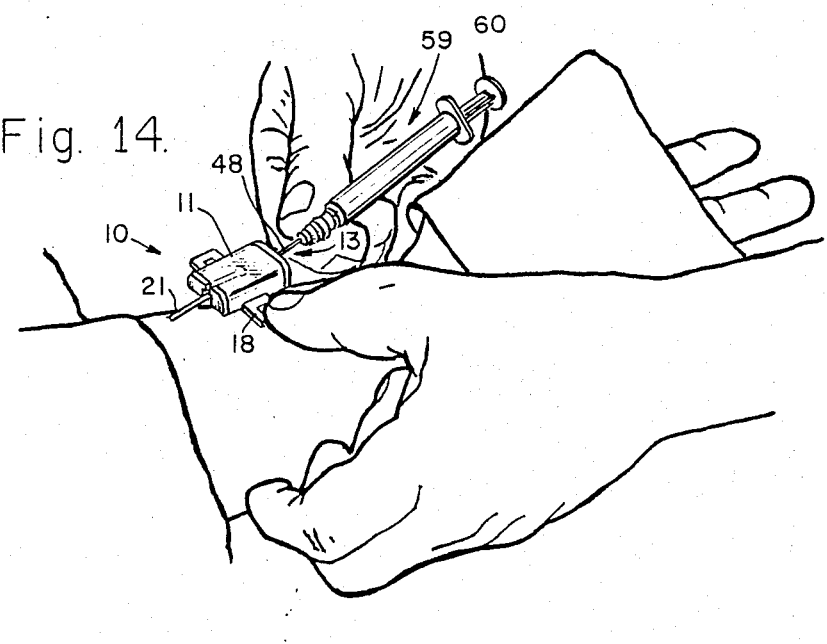

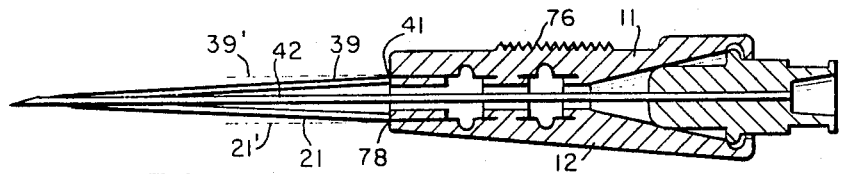
Fig. 30. Fig. 23.
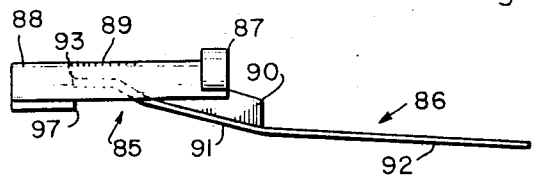
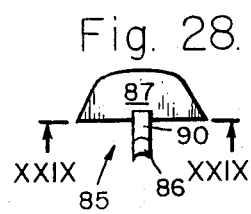
Fig. 28.
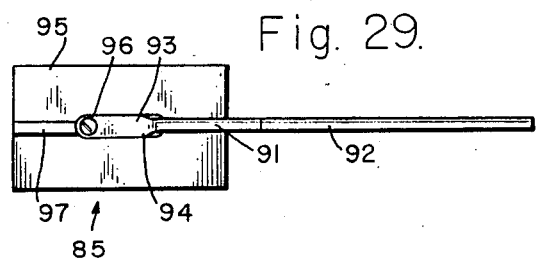
Fig. 29.
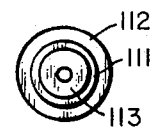
Fig. 35.
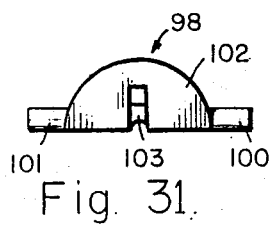
Fig. 31.
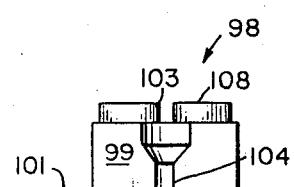
Fig. 33.
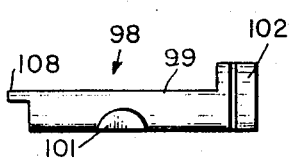
Fig. 34.
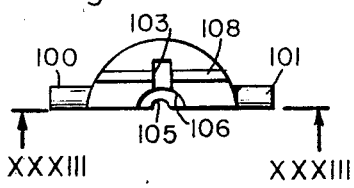
Fig. 32.
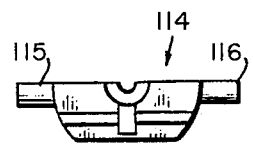
Fig. 36.
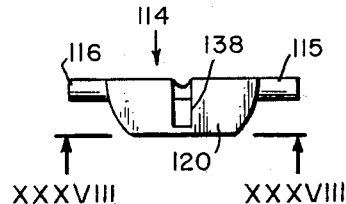
Fig. 37.
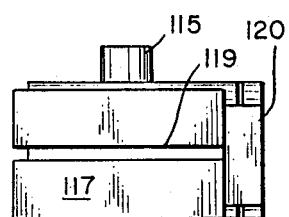
Fig. 38.

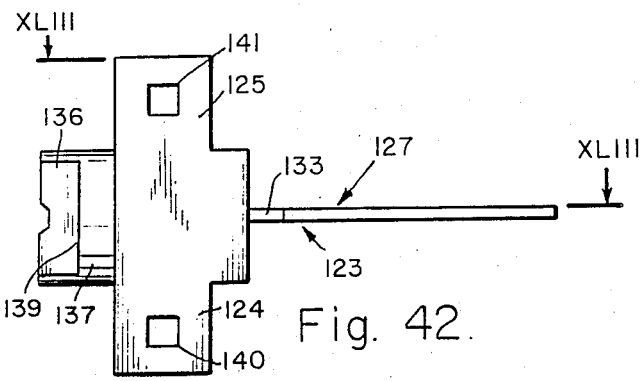
Fig. 42.
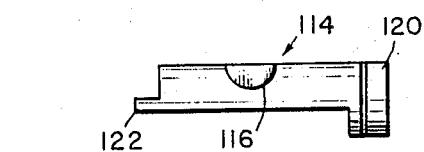
Fig. 39.
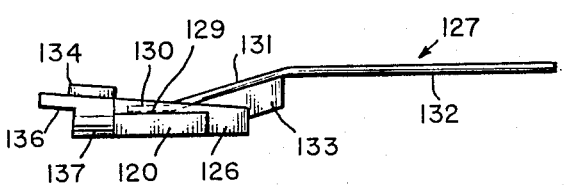
Fig. 43.
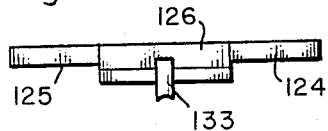
Fig. 40.
Fig. 41.
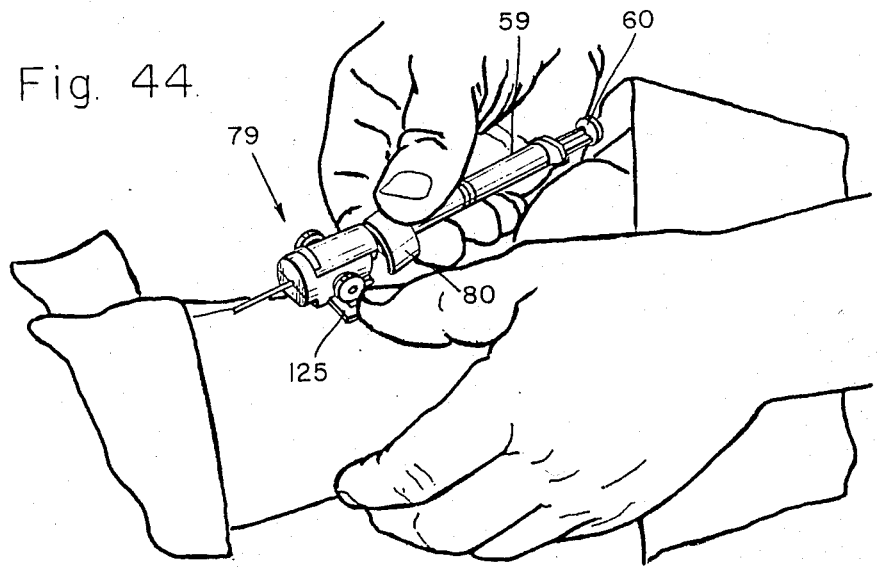
Fig. 44.

TUBE INSERTION APPARATUS

BACKGROUND OF THE INVENTION

1. Field of the Invention

The invention relates to surgical and medical devices; and, more particularly, to apparatus for aiding in the insertion of tubes of various sizes into a patient.

2. Description of the Prior Art

In U.S. Pat. No. 3,817,250, there is described an instrument for performing a tracheostomy and other surgical procedures. Another such device is described in my U.S. Pat. No. 3,688,773. There is need for devices for inserting tubes, such as catheter tubes, of varying lengths, into a patient. Also, in such prior art devices for accomplishing the same, intravenous catheter embolization can occur if the area of penetration is not sealed. There is need for a device for inserting catheter tubes or the like of varying diameters which can seal off the area of penetration, which can be used to attach sutures or the like for stabilization and allow smooth penetration of the needle and straight line insertion of a catheter.

SUMMARY OF INVENTION

It is an object of this invention to provide apparatus for insertion of tubes of various diameters into a patient.

It is a further object of this invention to provide apparatus for assistance of the insertion of catheter tubes into a patient.

These and other objects are preferably accomplished by providing mating upper and lower needle portions, the lower portion being flattened on the bottom surface for abutment with the body of the patient with tabs extending outwardly on both sides of the mating portions also adapted to abut against the body of the patient. The two mating portions are removably secured together so that the mating needle halves form an elongated cylindrical needle extending outwardly from one side of the secured portions and the mating portions forming a slot on the other side for receiving the luer adapter of a stylet therein.

BRIEF DESCRIPTION OF THE DRAWING

FIG. 3 is an exploded view of the apparatus of FIGS. 1 and 2;

FIG. 8 is a bottom plan view of the portion 11 of the device shown in FIG. 3;

FIG. 9 is a side view of the portion 11 of the device shown in FIG. 3;

FIG. 10 is a perspective view of the apparatus of FIG. 1 illustrating the mating of the upper and lower housing portions;

FIG. 11 is a view taken along lines XI—XI of FIG. 1;

FIG. 12 is a view taken along lines XII—XII of FIG. 1, the stylet being removed for convenience of illustration except for a dotted line representation of a portion thereof;

FIGS. 13 through 15 and 18 through 22 are progressive illustrative views illustrating the use of the apparatus of FIGS. 1 to 12;

FIG. 23 is a side view of the assembled parts of the embodiment of FIGS. 1 to 12;

FIG. 28 is a view take along lines XXVIII—XXVIII of FIG. 24;

FIG. 29 is a view taken along lines XXIX—XXIX of FIG. 28;

FIG. 30 is a side view of the housing portion 85 of FIG. 24;

FIGS. 31 and 32 are views taken along lines XXXI—XXXI and XXXII—XXXII of FIG. 24, respectively;

FIG. 33 is a view along lines XXXIII—XXXIII of FIG. 32;

FIG. 34 is a side view of the part 98 of FIG. 24;

FIG. 35 is a view taken along lines XXXV—XXXV of FIG. 24;

FIGS. 36 and 37 are views taken along lines XXXVI—XXXVI and XXXVII—XXXVII of FIG. 24, respectively;

FIG. 38 is a view taken along lines XXXVIII—XXXVIII of FIG. 37;

FIG. 39 is a side view of the part 114 of FIG. 24;

FIGS. 40 and 41 are views taken along lines XL—XL and XLI—XLI of FIG. 24, respectively;

FIG. 42 is a view taken along lines XLII—XLII of FIG. 41;

FIG. 43 is a view taken along lines XLIII—XLIII of FIG. 42; and

FIGS. 44 through 49 are views illustrating the various steps in using the apparatus of FIGS. 24 through 43.

DESCRIPTION OF THE PREFERRED EMBODIMENT

Figure 1:
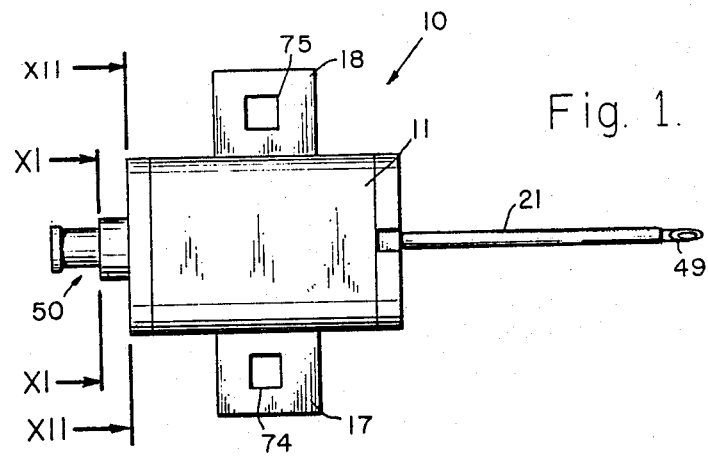
FIG. 1 is a top plan view of apparatus in accordance with the teachings of the invention.
Figure 2:
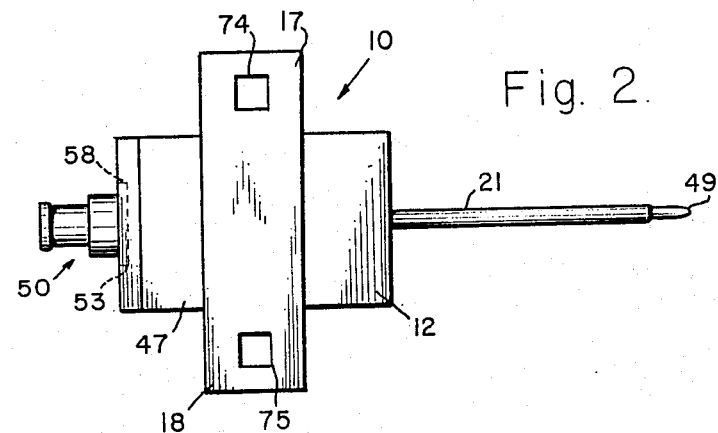
FIG. 2 is a bottom plan view of the apparatus of FIG. 1.

Referring now to FIG. 1 on the drawing, apparatus 10 is shown in assembled form (see also FIG. 2). Apparatus 10 is comprised of upper and lower mating needle half housing portions 11, 12, respectively. As seen in FIG. 3, a stylet 13 completes the apparatus 10. Lower portion 12 has a front wall 14 with a space 15 therebetween extending upwardly from base 16. A pair of laterally extending tabs 17,18 extend outwardly from both sides of base 16. Base 16 has an elongated groove 19 (FIG. 3) on its upper surface extending longitudinally from the front (to the right in FIG. 3) along substantially the central axis thereof and terminating at the rear adjacent a wider groove 20 (see also FIG. 5). A needle half 21, arcuate in cross-section, has a first straight portion 78 (see also FIG. 23) and is secured, via screw 23 or the like, in groove 19 extending outwardly therefrom then angling upwardly as seen in FIG. 23.

Figure 7:
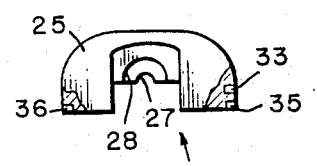

As seen in FIG. 3, the upper housing portion 11 has a main housing portion 22 having downwardly curved sides 23,24, respectively, and closed off at the rear by a U-shaped wall portion 25 (see FIG. 7). As seen in FIG. 3, both portions 22 and 16 are transparent so that the interior components are visible for reasons to be discussed. Of course, it is not critical to the invention that these parts be transparent.

Figure 6:
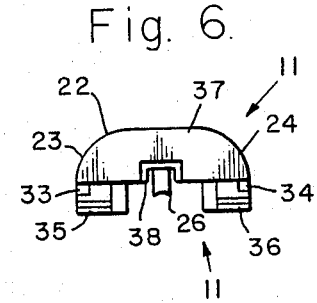

As seen in FIG. 8, a groove 26 extends from the right (to the right in FIG. 8) along the bottom central axis of portion 22 coincident with a wider groove 27, which is preferably also deeper than groove 26, opening at a circular groove 28. Groove 28 opens into a chamber 29 having a tapered wall 30 and end portions 31,32, FIG. 8, of U-shaped wall portion 25 extending inwardly on both sides of chamber 29. Side rails 33,34 (FIGS. 6 and 8) extend along the bottom of arcuate sides 23,24, respectively, and tabs or ears 35,36 extend inwardly from the bottom of each side of wall portion 25 spaced from rails 33,34, respectively, as seen in FIGS. 7 and 9. As seen in FIG. 3, rails 33,34 extend a short distance beyond the end facing wall 37 (see also FIG. 6) as does a portion 38 of housing portion 22 (extending from wall 37) forming groove 26. An arcuate needle half 39 is secured, as by screw 40, in grooves 26 and 27 and extending outwardly as seen in FIGS. 3 and 8. Also, as seen in FIG. 9, needle half 39 has a first straight portion 41 within groove 27, then an outwardly and downwardly angled portion 42 (FIG. 9).

Figure 4:
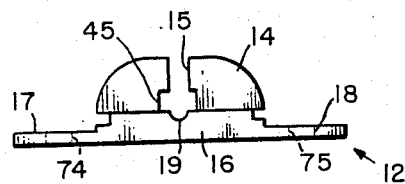
FIGS. 4 through 7 are views taken along lines IV—IV, V—V, VI—VI, and VII—VII of FIG. 3, respectively, FIG. 7 being partly in section.
Figure 5:
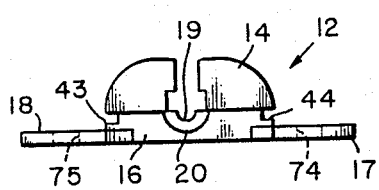

As seen in FIG. 10, upper housing portion 11 is assembled to lower housing portion 12 by insertion of needle half 39 through the opening 15 down into mating engagement with needle half 21 in groove 19. At the same time, rails 33,34 ride along side tracks 43,44, respectively, formed on each lower side of base 16 as seen in FIGS. 3 and 5. Portion 38 friction fits into the wider lower portion 45 of opening 15 (FIG. 4) in lower portion 12. It can also be seen in FIGS. 4 and 23 that lower portion 12 is flat and tapered on its bottom surface for reasons to be discussed. The facing wall 37 abuts against the rear of wall 14 and the tabs 35,36 enter notches 46,47, respectively, (FIGS. 2 and 5) cut out of the bottom rear end of base 16. The final assembled parts 11 and 12 are shown in FIGS. 1 and 2.

Referring again to FIG. 3, the conventional stylet 13 has a hollow elongated needle 48, terminating in sharpened point 49, extended from a conventional luer adapter 50.

Adapter 50 has main body portion 51, which may be cylindrical, integral with a second body portion 52, which may also be cylindrical, separated by a flange 53 (see also FIG. 11) which may be an elongated oval with flattened sides, and a third body portion 54 integral with main body portion 51 extending rearwardly therefrom and terminating in a square shaped flange 55. Portion 54 may also be cylindrical and both portions 52 and 54 may be of lesser outer diameter than main body portion 51. A throughbore 56 (FIG. 11) extends through the adapter 50 fluidly communicating with hollow needle 48.

In assembling this stylet 13 to the connected upper and lower housing portions 11,12, the portions 11,12 are assembled as heretofore discussed with respect to FIG. 3. Needle 48 is now inserted into the opening formed by the mating assembly of upper and lower portions 11,12 as seen in FIGS. 5 and 7. This can be seen in FIG. 12 where groove 19 mates with groove 27 to form a hole. The flange 53 of the luer adapter 50 is aligned with the arcuate opening 57 (FIG. 12) in wall portion 25 and needle 48 enters between needle halves 21,39 separating the same with point 49 exiting thereout as seen in FIG. 1. Leur adapter 50 is now rotated so that flange 53 extends transverse to opening 57 as seen in FIG. 2 and in dotted lines in FIG. 12.

It is to be understood that flange 53 is generally configured to opening 57 and the width thereof is related to the space 58 (FIG. 2) formed between wall 25 and the terminal end of lower portion 12 to be retained therein. The final assembly is shown in FIGS. 1 and 2.

The operation of apparatus 10 will now be described with reference to FIGS. 13 through 15 and 18 through 22. As seen in FIG. 13, a conventional syringe 59 having an obturator 60 is coupled to luer adapter 50 as is well known in the art. Needle point 49 is used to pierce the arm 61 of the patient, the obturator 60 being withdrawn to determine the degree of penetration as is well known in the art. It can be seen that the thumb 62 of the surgeon pressed down on the tab 18 to hold apparatus 10 against the skin of the patient, the flat tapered bottom of lower portion 12 being disposed adjacent the patient's skin.

The syringe 59 and stylet 13, connected together, are withdrawn (FIG. 14) from mating portions 11,12, needle 48 coming out of its position between needle halves 21,39. The surgeon continues to hold stabilizing tab 18 against the patient.

Figure 15:
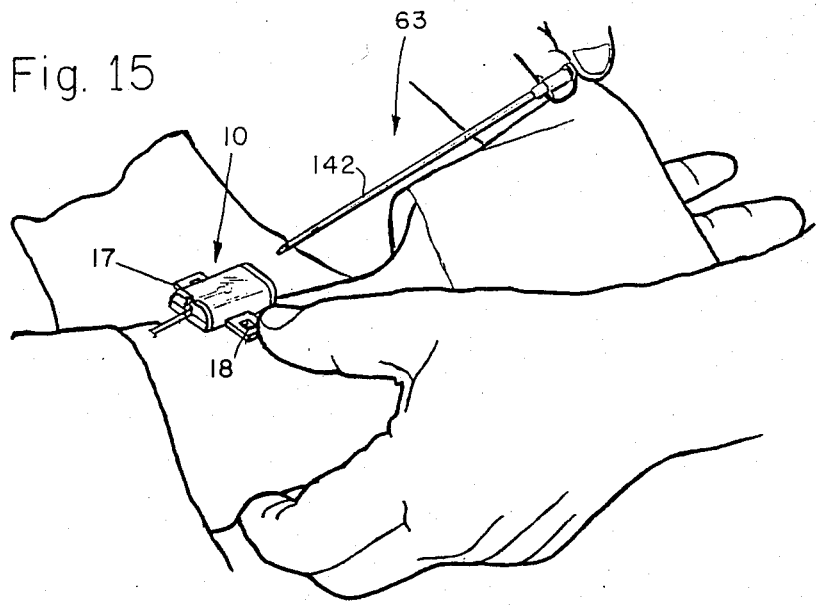
Figure 16:
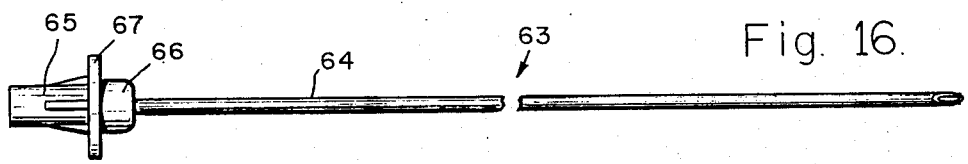
FIGS. 16 and 17 are top plan views of the two parts of the catheter of FIG. 15.
Figure 17:
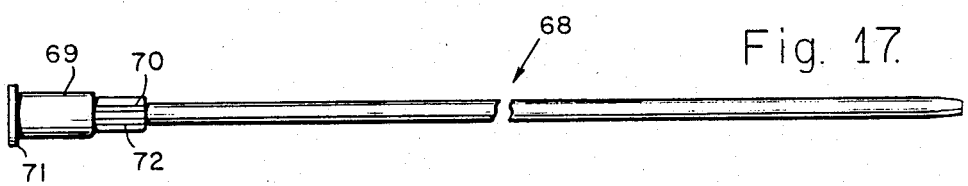

As seen in FIG. 15, the surgeon continues to hold stabilizing tab 18 after removal of syringe 59 and stylet 13 and now inserts a conventional catheter 63. Catheter 63 is comprised of two parts as seen in FIGS. 16 and 17. As seen in FIG. 16, an elongated hollow tube 64, of any suitable rigid material such as metal, extends from a hollow main tubular housing 65 connected by an extension portion 66 separated from housing 65 by circular flange 67. Catheter 63 is also comprised of elongated hollow tube 68, of a flexible material such as plastic, extending from a hollow main housing 69 connected thereto by an extension portion 70 and terminating at the rear end in flange 71. Extension portion 70 may be ribbed or roughened, as seen in ribs 72, on its outer surface and of a lesser outer diameter that the outer diameter of portion 69.

Tube 64 is adapted to be inserted into the interior of tube 69 through portions 69,70 until flange 67 abuts against flange 71, the overall length of tube 64 being related to the overall length of tube 69. The final assembly is shown in FIG. 15.

Figure 18:
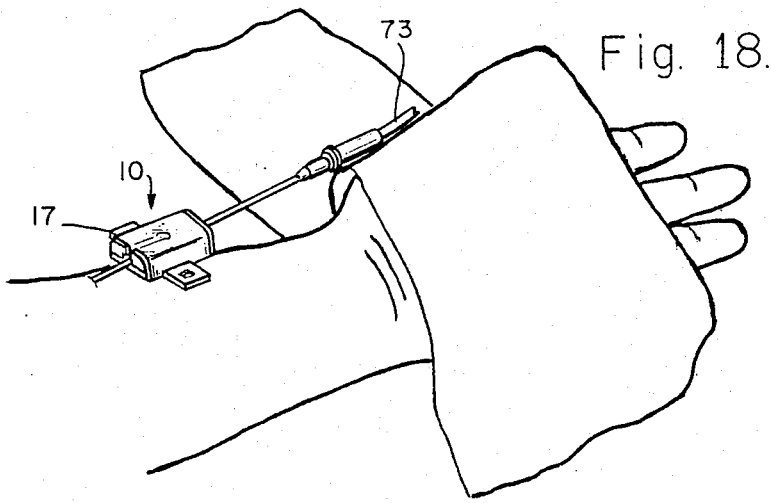

Referring again to FIG. 15, catheter tubes 64,68 are inserted through opening of throughbore 56 (FIG. 11) and through needle halves 21, 39 down into the vein of the patient and the housing 65 may be coupled to a tube 73 leading to a bottle (not shown) FIG. 18.

Figure 19:
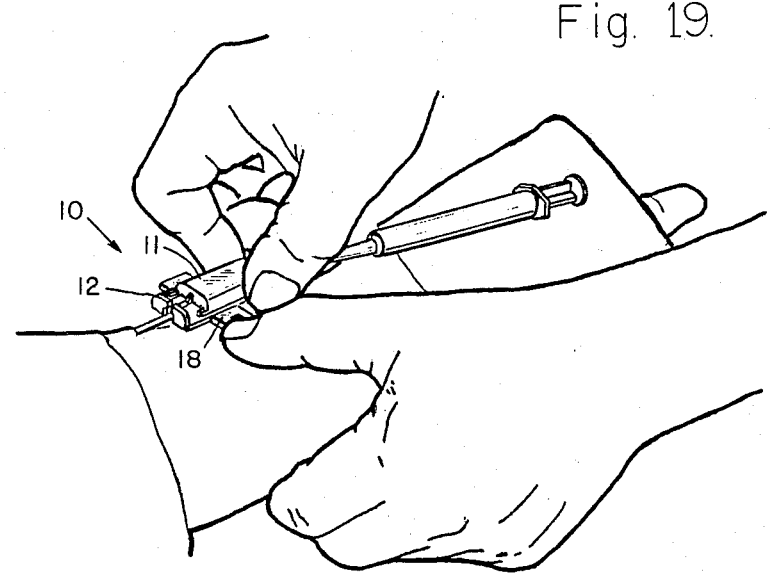
Figure 20:
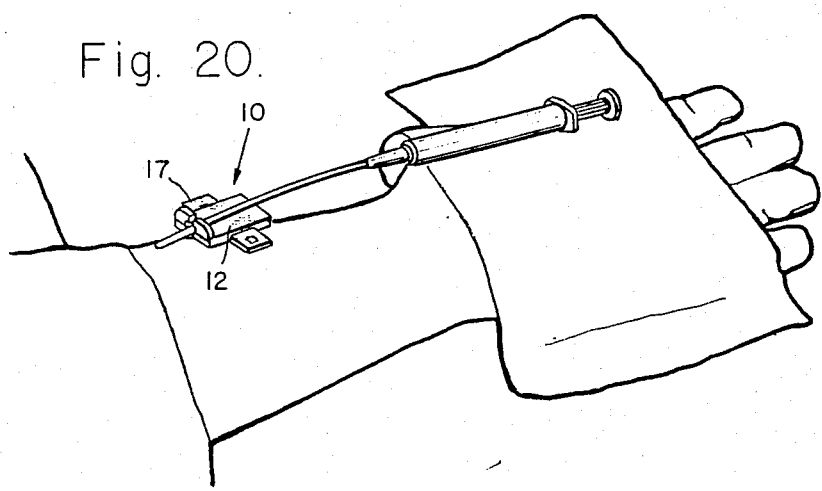
Figure 21:
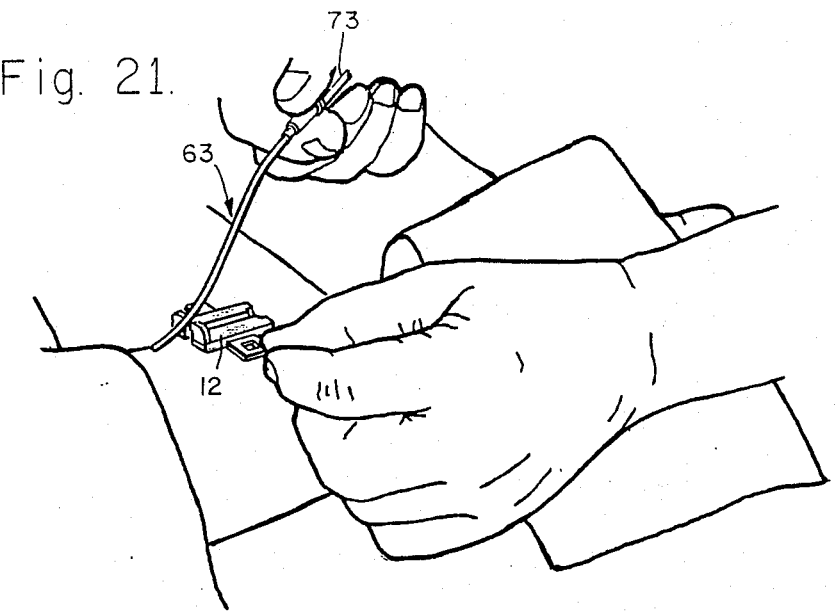
Figure 22:
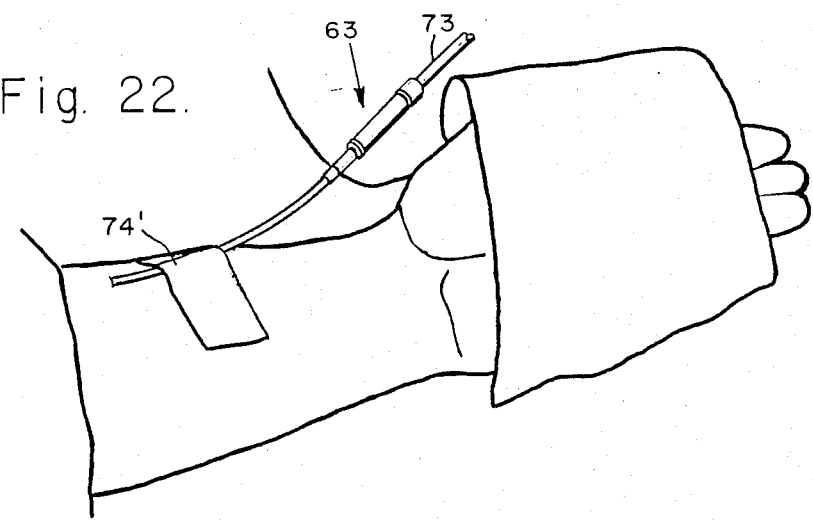

If desired, as seen in FIG. 19, the portions 11,12 may be removed by holding tab 18 and sliding the upper portion 11 off of lower portion 12 (see FIG. 20). Lower portion 12 may now be removed (FIG. 21) and catheter 63 taped via tape 74' to the patient (FIG. 22). Of course, as seen in FIGS. 18 and 20, either the two portions 11,12 or lower portion 12 may be kept in place if desired by merely taping the tabs 17,18 to the patient's arm or providing holes or the like, such as holes 74,75, respectively, in the tabs 17,18 for connecting elongated tie members thereto. Also, the upper surface of upper housing portion 11 may be knurled or roughened, as at knurls 76, to assist in grasping the same (FIG. 23).

As particularly seen in FIG. 23, the fact that the two needle halves extend first parallel than angle toward each other ensures that the same do not overexpand, that is, go beyond their parallel position. A large tube can go between the needle halves 21,39 and the needle halves 21,39 will not expand beyond the parallel indicated by dotted lines 21',39' (coincident with needle portions 78,41, respectively).

Figures 24, 25, 26, 27:
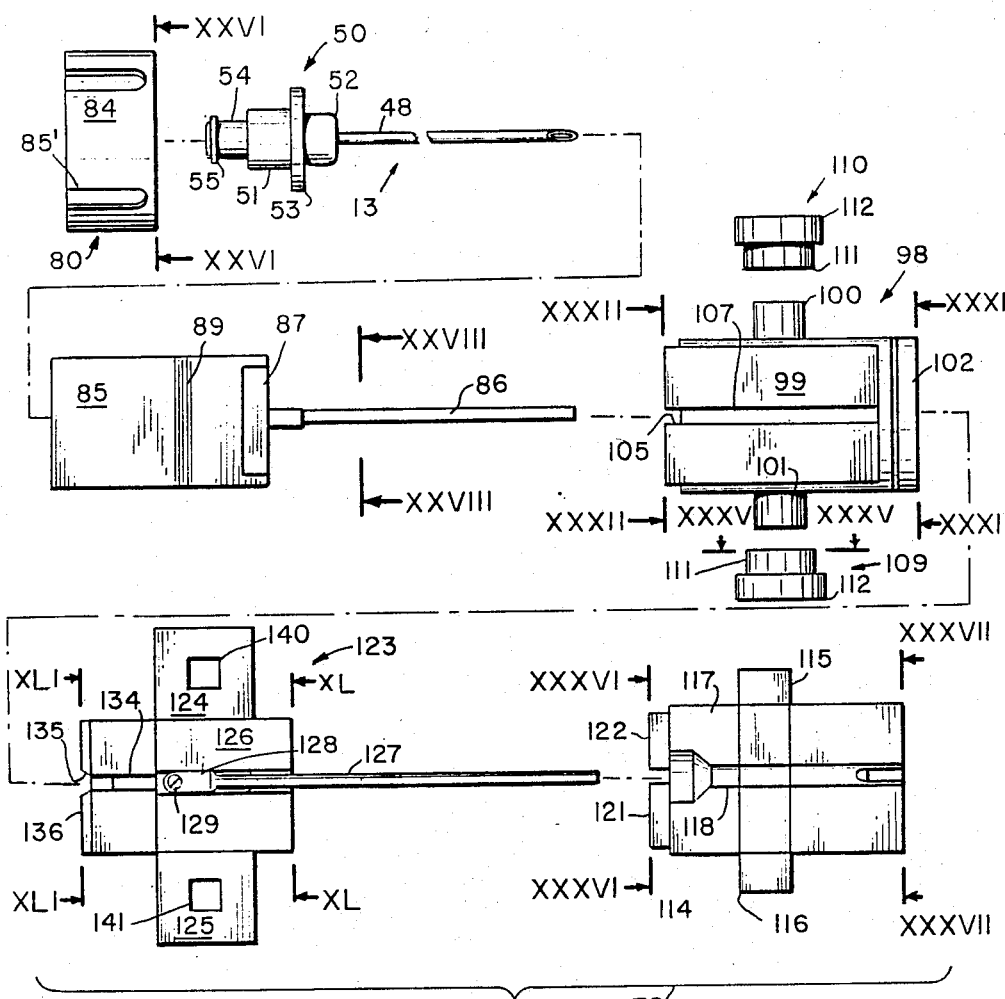
FIG. 24 is an exploded view of another embodiment of the invention.
FIG. 25 is an assembled plan view of the embodiment of FIG. 24.
FIGS. 26 and 27 are views taken along lines XXVI—XXVI and XXVII—XXVII of FIGS. 24 and 26, respectively.

The foregoing has described a preferred embodiment of the invention. However, as seen in FIGS. 24 and 25 wherein like numerals refer to like parts of the embodiment of FIGS. 1 to 23, the assembly, instead of being two mating parts, may be comprised of a plurality of parts as seen in the exploded view of assembly 79 in FIG. 24. The assembled parts of assembly 79 are shown in FIG. 25. Thus, in this embodiment, an end cap 80 is provided with an arcuate configuration with a back wall 81 (FIG. 26) with aperture 82 therethrough. As seen in FIG. 27, a bottom wall 83 closed off a portion of the bottom of the curved wall 84. One or more grooves 85' (FIG. 24) may be provided in the exterior of wall 84. A stylet 13, which is identical to the stylet of the embodiment of FIGS. 1 to 23, is provided and like numerals refer to like parts of FIG. 3.

A top housing portion 85 (FIG. 24) is provided having an upper needle half 86 (identical to needle half 21 of the embodiment of FIGS. 1 to 23) extending from housing portion 85. Housing portion 85 has an arcuate forward flange 87 (see particularly FIG. 30) which extends above the upper curved surface 88 of body portion 85 which may be roughened or knurled, as at knurls 89. A forwardly and downwardly extending flat needle half support 90 (FIG. 30) extends from and is integral with the lower front portion of housing portion 85. As seen in FIG. 30, this support 90 follows the angle of a first angled portion 91 of needle half 86 between forward straight portion 92 and a flat rear portion 93 (FIG. 29) disposed in a groove 94 in the undersurface 95 of housing portion 85 and retained therein by screw 96. A guide flange 97 (see also FIG. 30) extends from groove 94 along the central axis of housing portion 85 and downwardly. As can be seen in dotted lines in FIG. 30, needle half portion 93 lies along a plane generally parallel to the plane of needle half portion 92 for reasons to be discussed.

A first or upper middle housing portions 98 is provided having a main body section 99 and arcuate side tabs 100,101, respectively. An arcuate flange 102 (FIGS. 31 and 34) is provided at the forward end of section 99 extending upwardly therefrom. A slot 103 is provided in flange 102. An elongated groove 104 (see particularly FIG. 33) is provided along the upper surface of section 99 communicating at one end with a notch 105 at the rear terminal end of section 99. Groove 104 and notch 105 extend along the central axis of section 99 and an arcuate cut out area or section 106 is provided in the underside of section 99 surrounding notch 105. A like groove 107 (FIG. 24) is also provided along the upper surface of section 99. As particularly seen in FIG. 34, a flange 108 extends rearwardly from the terminal end of the upper wall of section 99, notch 103 cutting therethrough as seen in FIG. 32.

A pair of securement caps 109,110 (FIG. 24) are provided, each cap being identical and having a first hollow cylindrical section 111 integral with a second hollow cylindrical section 112, the latter closed off by an apertured rear wall 113. These caps, as seen in FIG. 25, are of a size to fit over mating arcuate tab portions of the parts of FIG. 24 as will be discussed.

Looking again at FIG. 24, the lower or second middle section 114 has a pair of tabs 115,116 extending outwardly on opposite sides of body section 117, these tabs being semi-circular in cross-section (FIG. 39). As seen in FIG. 24, a groove 118 extends along the central axis of the upper surface of body section 117 and, as seen in FIG. 38, a like groove 119 extends along the bottom surface of body section 117 to and terminating at an arcuate flange 120 (FIG. 37) extending below the plane of the lower surface of body section 117 as clearly seen in FIGS. 37 and 39. A notch 121 (see FIG. 24) is provided on the upper surface of body section 117 along the axis of groove 118 and a flange or lip 122 extends rearwardly from the plane of the lower surface of body section 117 as clearly seen in FIG. 24.

The third or middle section 123 (FIG. 24) has a pair of side tabs 124,125 extending on opposite sides of body section 126. A needle half 127 is secured in a groove 128 in the upper portion of body section 126 extending along the central axis thereof, a screw 129 or the like securing needle half 127 in place. As seen in dotted lines in FIG. 43, needle half 127 has a first linear portion 130 extending from screw 129, a second downwardly extending angled integral portion 131 and a third integral portion 132 extending generally parallel to first portion 130. A flange 133 (see also FIGS. 40,42 and 43) extends upwardly from the upper surface of body section 126 (or downwardly when oriented as in FIG. 43) at an angle related to the angularity of needle half portion 131 to provide a support thereof. As seen in FIG. 43, a flange 134 extends downwardly from the underside of body section 126 as oriented in FIG. 43 (or upwardly in the view shown in FIG. 24). A notch 135 is provided at the rear end of body section 126 and the rear portion 136 (FIGS. 24 and 43) of body section 126 is of a reduced thickness with the remainder of body section 126, the portion 137 adjacent thereto being arcuate in cross-section as seen in FIG. 41.

The assembly of the components of the devices of FIGS. 24 to 43 will now be described, the parts being oriented as in FIG. 24. Top housing portion 85 is first placed on top of middle upper housing portion 98 with needle half 86 inserted through slot 103 (FIG. 31) until flange 90 enters the slot 103 and the forward face of flange 87 abuts against the rear face of flange 102, the lower surface of portion 85 abutting against and mating with the upper surface of main body section 99. Lower middle section 114 is now place under the lower surface of main body section 99, flush therewith the arcuate shaped tabs 100,101 and 115,116 mating to form a cylindrical tab. End caps 109,110 are now press-fit onto the mating tabs and needle half 127 of lower middle section 123 is now inserted into slot 138 (FIG. 37) of section 114 until flange 133 rides along groove 119 and enters said slot 138 nd the front face of section 126 abuts against the rear face of flange 120, flange 133 being disposed in slot 138. The needle halves 86,127 at their forward ends are in a juxtaposed position forming a hollow cylindrical tube. Stylet 13 is now inserted rearwardly through the hold formed by the mating grooves of sections 98 and 114, the stylet needle 48 entering between mating needle halves 86,127 with flange 53 entering the arc between mating sections 85 and 123 defined by the rear end of curved surface 88 and flange 122 of section 114 surrounding the hole formed therebetween.

Cap 80 is now placed over the rear end of the four mating assembled sections 85,98,114 and 123, bottom wall 83 abutting against the wall 139 (FIG. 42) formed at the intersection of portions 136 and 137 and the luer adapter 50 extending through aperture 82 and rearwardly as seen in the final assembled view shown in FIG. 25.

Figure 45:
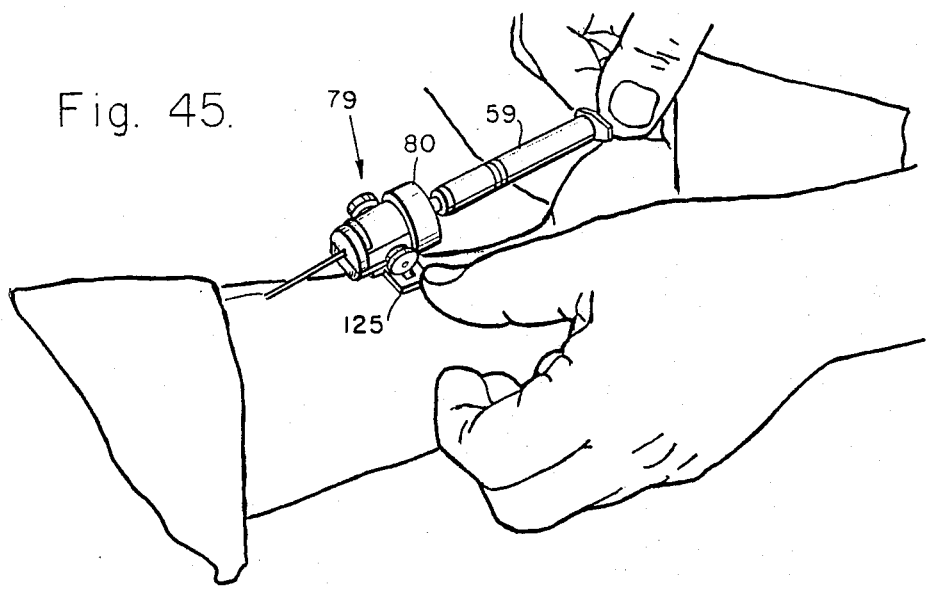
Figure 46:
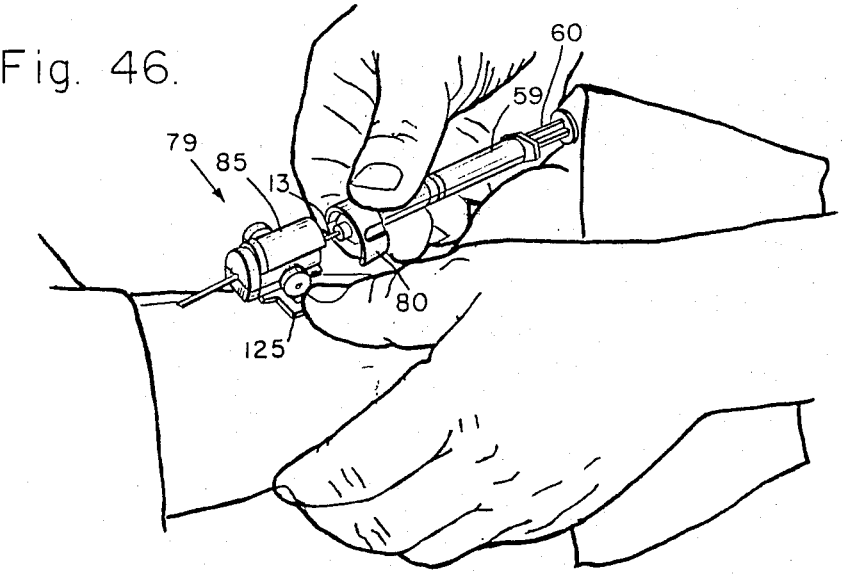
Figure 47:
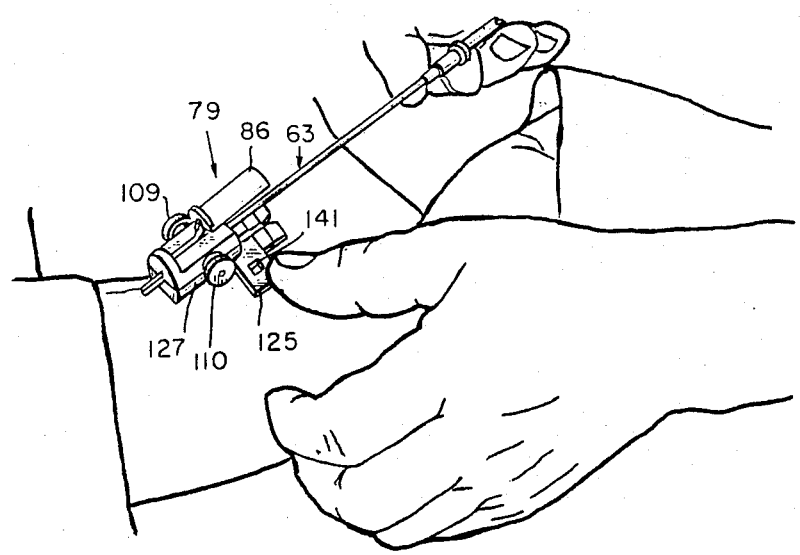
Figure 48:
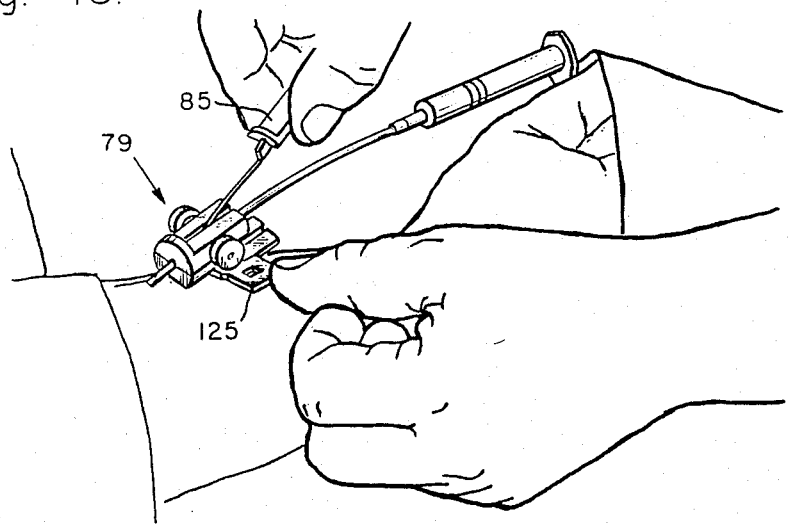

The use of apparatus 79 will now be described and is essentially identical to the use of apparatus 10 and reference may be made to the description of FIGS. 13 through 15 and 18 through 22 for a complete understanding of the invention. Briefly, as seen in FIG. 44, a syringe 59 having an obturator 60 is connected to apparatus 79 as previously discussed and the needle is inserted into the body of the patient, the surgeon holding at least one of the tabs, as tab 125, down against the body of the patient and grasping apparatus 79 at the rear closure cap 80. As seen in FIG. 45, the obturator 60 is withdrawn to determine the degree of penetration. In FIG. 46, the end cap 80 and syringe 59 with its obturator 60 is removed along with stylet 13 while the surgeon holds down the apparatus 79 via tab 125. The surgeon continues to hold down tab 125 and top housing portion 85 can be withdrawn slightly (FIG. 47) to assist in the insertion of the catheter 63 between needle halves 86,127. Prior to insertion of the catheter 63, the tabs 124,125 can be held and the body portion pushed forward by grasping caps 109,110 to seal the penetration point against air or blood leakage. Top housing portion 85 is now withdrawn (FIG. 48) by sliding it off and removing the same while continuing to support apparatus 79 by holding down on tab 125.

Figure 49:
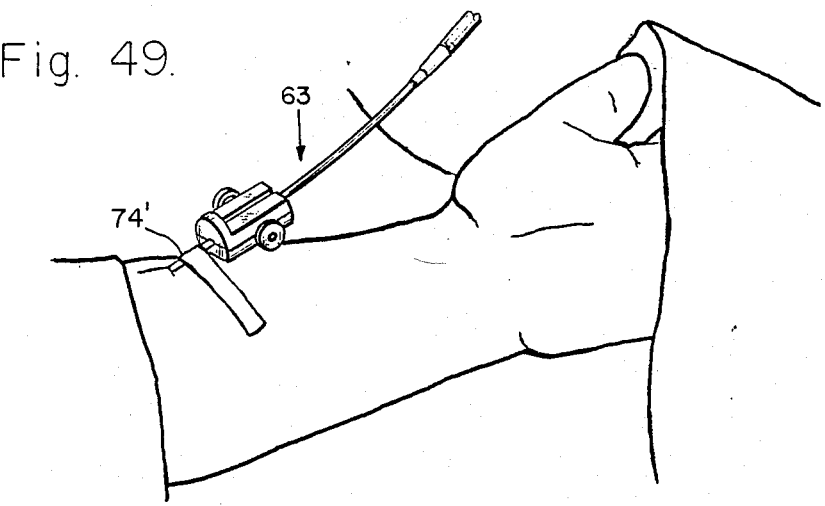

As seen in FIG. 49, the catheter may be taped to the arm of the patient and the remaining interconnected parts left in place. Alternatively, as discussed herein above with respect to the discussion of FIGS. 21 and 22, apparatus 79 can be removed merely by removing caps 109,110 and then parts 98,123 and 114 resulting in the identical set up shown in FIG. 22. Of course, slots or opening 140,141 may be formed in tabs 124,125, respectively, FIGS. 24 and 42, of body portion 123 for receiving tie down means, as previously discussed, for securing body portion 123 to the arm of the patient.

It can be appreciated that the angularity of the needle halves of both embodiments accommodates tubings of various diameters due to the expandability of the needle halves. Both embodiments, which allow for needle halves expansion in two different ways also allow for rapid blood insertion (hyper infusion) when needed.

In both embodiments, the catheter can be marked to show the depth of penetration. That is, as seen in FIG. 15, catheter 63 can be marked at index line 142 to show that the catheter 63 has been extended to the needle tip in the vein.

In both embodiments, the obturator of the catheter is removed and the catheter is connected to an IV bottle for drainage or fluid insertion.

The invention herein can be used with IV catheters of varying lengths, e.g., 1 inch to 3 inches, various types, as in venous punctures of the peripheral and central venous pressure type. It can also be used with peripheral arterial puncture-type catheters. It can be used in intrathoracic catheters inserted into chests and catheters for peritoneal cavities. It can be used in many other operations that may occur to one skilled in the art, such as intraspinal, intraosseous, joint aspiration, urology, dilation of cervix, fenestrations, orthopedic operations, kidney stone operations, transtracheal procedures, etc.

It can be seen that the inventions herein has significant advantages over prior art devices. The upper body portions on both embodiments slide forward to seal the area of penetration. The needle halves do not contact each other and are hinged so that the spreading apart thereof accomodates any suitable dimensions and needle half lengths. The structure of both embodiments results in a tapered rear opening aligned with the center of the apparatus to assist in tube insertion.

It can be seen that there is described apparatus for inserting tubes of varying sizes in carrying out a wide variety of operations.

The spreading apart of the needle halves approximates the parallel so that their tips do not overexpand, can accommodate tubes of varying sizes and produce tension at the needle half tips for smooth penetration Since the undersurface of both embodiments is tapered, the needle half tips won't lift up damaging the tissue but remain in line with the original needle penetration angle.

All parts can be made of any suitable materials, such as plastic, which may be transparent to view the blood in the interior thereof, steel, etc. and can be of any suitable dimensions and needle half lengths. The invention is not to be limiting by the forgoing description which is for illustrative purposes only, but the scope of the invention is defined by the appended claims.

I claim:

1. A device for inserting tubes of varying sizes into the body of a patient comprising:

at least a first upper needle half housing portion having a first elongated needle half arcuate in cross-section with a rear end secured to said upper needle half housing portion;

at least a second lower needle half housing portion having a second elongated needle half arcuate in cross-section with a rear end secured to said lower needle half housing portion, said lower needle half housing portion being flattened in the bottom for abutment against the skin of the patient;

removable securement means associated with both needle half housing portions for removably securing the same together so that the mating needle halves meet at mating surfaces and form a cylindrical elongated needle receiving member extending from the secured portions, and said needle half housing portions also meeting at mating surfaces, said first elongated needle half including a first straight portion secured to said upper needle half housing portion at a point remote from the mating surfaces of said upper and lower needle half housing portions and extending generally parallel to the central axis thereof along an elongated axis spaced from the mating surfaces of said upper needle half housing portions, said first needle half also having a second angled portion integral with said first portion extending away from said first portion and beyond said upper needle half housing portion, said second elongated needle half including a first straight portion secured to said lower needle half housing portion at a point remote from the mating surface of said lower needle half housing portion and extending generally parallel to the central axis thereof along an elongated axis spaced from the mating surface of said lower needle half housing portion, said second needle half also having a second angled portion integral with said first portion of said second needle half extending from said first portion of said second needle half and beyond said lower needle half housing portions, each of said first and second angled portions extending toward each other, whereby the mating needle halves extending out of the upper and lower housing portions move to a mating position with their rear ends fixed in firm position in said respective upper and lower housing portions, and a keying slot formed by the securement of said needle half housing portions opposite the end thereof from which said needle halves extend for receiving the luer adaptor of a stylet therein.

2. In the device of claim 1 including a pair of stabilizing tabs extending outwardly from opposite sides of said lower needle half, housing portion.

3. In the device of claim 2 wherein said tabs are apertured.

4. In the device of claim 1 wherein the outer surface of said upper needle half housing portion is roughened.

5. In the device of claim 1 wherein said keying slot includes an opening at the rear of said upper housing portion defined by an end wall thereon with a space formed therein for receiving said luer adapter and locking the same therein.

6. In the device of claim 1 wherein said body potions are of transparent material.

7. In the device of claim 1 wherein the undersurface of said lower portion is tapered.

8. In the device of claim 1 wherein said removable securement means includes said upper portion being slidably mounted on said lower portion.

9. In the device of claim 8 wherein said upper portion is slidably mounted to said lower portion by mating tracks on both said portions.

10. In the device of claim 9 including at least one inwardly extending tab on the bottom of said upper portion extending inwardly toward the center thereof and underlying at least a portion of the bottom of said lower portion when said upper portion is slidably mounted to said lower portion whereby said tab holds said lower portion to said upper portion until said lower portion is slightly retracted away from said upper portion in a direction opposite that of said extent of said tab.

11. In the device of claim 1 wherein said lower portion has a frontal wall with said needle half extending therefrom along substantially the center axis thereof and an aperture through said frontal wall vertically above the point where said needle half extends for receiving therethrough the needle half of said upper housing portion.

12. In the device of claim 1 including a mating pair of middle body portions having outwardly extending bosses semi-circular in cross-section forming a cylinder when assembled to each other in abutting relationship, said upper and lower housing portions being secured to the upper and lower surfaces of said pair of middle body portions, respectively, when assembled, said needle halves extending through openings in said assembled middle body portions, said removable securement means including caps removably attached to said mating semi-circular bosses.

13. In the device of claim 12 wherein said removable securement means further includes an end cap enclosing said middle body portions and said upper and lower housing portions.

14. In the device of claim 13 wherein said keying slot is provided in said end cap.

15. A device for inserting tubes of varying sizes into the body of a patient comprising:
at least a first upper needle half housing portion having a first elongated needle half arcuate in cross-section;
at least a second lower needle half housing portion having a second elongated needle half arcuate in cross-section, said lower needle half housing portion being flattened in the bottom for abutment against the skin of the patient;
removable securement means associated with both needle half housing portions for removably securing the same together so that the mating needle halves form a cylindrical elongated needle receiving member extending from the secured portions, and a keying slot formed by the securement of said needle half housing portions opposite the end thereof from which said needle halves extend for receiving the luer adapter of a stylet therein, said removable securement means including said upper portion being slidably mounted on said lower portion and said upper portion being slidably mounted to said lower portion by mating tracks on both said portions.

16. A device for inserting tubes of varying sizes into the body of a patient comprising:
at least a first upper needle half housing portion having a first elongated needle half arcuate in cross-section;
at least a second lower needle half housing portion having a second elongated needle half arcuate in cross-section, said lower needle half housing portion being flattened in the bottom for abutment against the skin of the patient;
removable securement means associated with both needle half housing portions for removably securing the same together so that the mating needle halves form a cylindrical elongated needle receiving member extending from the secured portions, and a keying slot formed by the securement of said needle half housing portions opposite the end thereof from which said needle halves extend for receiving the luer adapter of a stylet therein, said lower portion having a frontal wall with said needle half extending therefrom along substantially the center axis thereof and an aperture through said frontal wall vertically above the point where said needle half extends for receiving therethrough the needle half of said upper housing portion.

17. A device for inserting tubes of varying sizes into the body of a patient comprising:
at least a first upper needle half housing portion having a first elongated needle half arcuate in cross-section;
at least a second lower needle half housing portion having a second elongated needle half arcuate in cross-section, said lower needle half housing portion being flattened in the bottom for abutment against the skin of the patient;
removable securement means associated with both needle half housing portions for removably securing the same together so that the mating needle halves form a cylindrical elongated needle receiving member extending from the secured portions, a keying slot formed by the securement of said needle half housing portions opposite the end thereof from which said needle halves extend for receiving the luer adapter of a stylet therein, and a mating pair of middle body portions having outwardly extending bosses semi-circular in cross-section forming a cylinder when assembled to each other in abutting relationship, said upper and lower housing portions being secured to the upper and lower surfaces of said pair of middle body portions, respectively, when assembled, said needle halves extending through openings in said assembled middle body portions, said removable securement means including caps removably attached to said mating semi-circular bosses.

18. In the device of claim 17 wherein said removable securement means further includes an end cap enclosing said middle body portions and said upper and lower housing portions.

* * * * *